(12) United States Patent
Van Neste et al.

(10) Patent No.: US 8,080,796 B1
(45) Date of Patent: Dec. 20, 2011

(54) STANDOFF SPECTROSCOPY USING A CONDITIONED TARGET

(75) Inventors: Charles W. Van Neste, Kingston, TN (US); Marissa E. Morales-Rodriguez, Knoxville, TN (US); Lawrence R. Senesac, Knoxville, TN (US); Thomas G. Thundat, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 12/828,064

(22) Filed: Jun. 30, 2010

(51) Int. Cl.
*G01J 5/00* (2006.01)
(52) U.S. Cl. ...................................... 250/338.1
(58) Field of Classification Search .......... 250/330–335, 250/336.1–336.2, 338.1–338.4, 339.01–339.15, 250/340, 341.1–341.8; 588/309; 436/164
See application file for complete search history.

(56) References Cited

U.S. PATENT DOCUMENTS

| | | | |
|---|---|---|---|
| 4,255,971 A | 3/1981 | Rosencwaig | |
| 4,276,780 A | 7/1981 | Patel et al. | |
| 4,543,486 A | 9/1985 | Rose | |
| 4,678,905 A | 7/1987 | Phillips | |
| 4,897,541 A | 1/1990 | Phillips | |
| 5,036,708 A | 8/1991 | Urban et al. | |
| 5,141,331 A | 8/1992 | Oehler et al. | |
| 5,285,677 A | 2/1994 | Oehler | |
| 5,319,977 A | 6/1994 | Quate et al. | |
| 5,360,268 A | 11/1994 | Hayashi et al. | |
| 5,391,001 A | 2/1995 | Rupert et al. | |
| 5,440,388 A | 8/1995 | Erickson | |
| 5,977,538 A | 11/1999 | Unger | |
| 6,006,593 A | 12/1999 | Yamanaka | |
| 6,066,295 A * | 5/2000 | Bernstein et al. | 422/50 |
| 6,400,449 B2 | 6/2002 | Maris et al. | |
| 6,466,806 B1 | 10/2002 | Geva et al. | |
| 6,630,111 B1 * | 10/2003 | Willson, III | 506/22 |
| 6,639,184 B1 | 10/2003 | Ennis | |
| 6,657,196 B2 | 12/2003 | Endo et al. | |
| 6,683,300 B2 * | 1/2004 | Doroshenko et al. | 250/288 |
| 6,831,747 B2 | 12/2004 | Ferrell et al. | |
| 7,091,254 B2 * | 8/2006 | Crivello | 522/1 |
| 7,207,206 B2 | 4/2007 | Pinnaduwage et al. | |

(Continued)

FOREIGN PATENT DOCUMENTS

DE     39 25 312 A1    4/1990

(Continued)

OTHER PUBLICATIONS

Graft et al., "UV gated Raman spectroscopy for standoff detection of explosives," 2008, Optical Materials, vol. 30, pp. 1739-1746.*

(Continued)

*Primary Examiner* — Kiho Kim
(74) *Attorney, Agent, or Firm* — Brinks Hofer Gilson & Lione

(57) ABSTRACT

A system and method are disclosed for standoff spectroscopy of molecules (e.g. from a residue) on a surface from a distance. A source emits radiation that modifies or conditions the residue, such as through photodecomposition. A spectral generating source measures a spectrum of the residue before and after the residue is exposed to the radiation from that source. The two spectra are compared to produce a distinct identification of the residues on the surface or identify certain properties of the residue.

20 Claims, 7 Drawing Sheets

U.S. PATENT DOCUMENTS

| | | | |
|---|---|---|---|
| 7,243,548 | B2 | 7/2007 | Thundat et al. |
| 7,245,380 | B2 | 7/2007 | Kosterev |
| 7,326,580 | B2 | 2/2008 | Fukushima et al. |
| 7,411,189 | B2 | 8/2008 | Kawakatsu |
| 7,442,922 | B2 | 10/2008 | Knebel et al. |
| 7,448,269 | B2 | 11/2008 | Shekhawat et al. |
| 7,605,922 | B2 | 10/2009 | Willing |
| 7,665,364 | B2 | 2/2010 | Su et al. |
| 7,691,583 | B2 | 4/2010 | Craighead |
| 7,838,869 | B2* | 11/2010 | Perera et al. ............... 257/21 |
| 2002/0125433 | A1* | 9/2002 | Endo et al. ............... 250/339.11 |
| 2002/0166969 | A1* | 11/2002 | Chou et al. ............... 250/339.08 |
| 2003/0052268 | A1* | 3/2003 | Doroshenko et al. ......... 250/288 |
| 2004/0085540 | A1 | 5/2004 | Lapotko et al. |
| 2004/0113077 | A1* | 6/2004 | Franzen et al. ............ 250/338.1 |
| 2004/0120577 | A1 | 6/2004 | Touzov |
| 2005/0070803 | A1 | 3/2005 | Cullum et al. |
| 2005/0117155 | A1 | 6/2005 | Kosterev |
| 2005/0201661 | A1 | 9/2005 | Loock et al. |
| 2005/0244747 | A1 | 11/2005 | Nagai et al. |
| 2007/0152154 | A1* | 7/2007 | DeCamp et al. ......... 250/339.07 |
| 2007/0175760 | A1 | 8/2007 | Thundat et al. |
| 2007/0220978 | A1 | 9/2007 | Su et al. |
| 2007/0220979 | A1 | 9/2007 | Su et al. |
| 2008/0094614 | A1 | 4/2008 | Tuschel et al. |
| 2008/0191137 | A1* | 8/2008 | Poteet et al. ............... 250/338.1 |
| 2008/0276695 | A1 | 11/2008 | Prater et al. |
| 2009/0174884 | A1 | 7/2009 | Kosterev et al. |
| 2009/0268200 | A1* | 10/2009 | Klug et al. ................. 356/301 |
| 2009/0321647 | A1 | 12/2009 | Shelley et al. |

FOREIGN PATENT DOCUMENTS

| | | |
|---|---|---|
| EP | 1 493 380 A1 | 1/2005 |
| JP | 11253794 A | 9/1999 |
| JP | 2001183294 A | 7/2001 |

OTHER PUBLICATIONS

*XI International Scanning Probe Microscopy Conference 2009—Poster Session*; (8 pages).

Tetard et al., *New modes for subsurface atomic force microscopy through nanomechanical coupling*; Nature Nanotechnology (Letters) (Dec. 20, 2009); www.nature.com/naturenanotechnology.

PCT Search Report and Written Opinion dated Dec. 14, 2009, PCT/US2009/052806, filed Aug. 5, 2009.

*Crossing the line: how aggressive cells invade the brain*; R&D Mag Nov. 6, 2009; pp. 1-3; www.rdmag.com/.

PCT Seach Report and Written Opinion dated Feb. 6, 2010, PCT/US2009/052820, filed May 8, 2009.

Van Neste et al., Standoff Detection of Explosive Residues Using Photothermal Microcantilevers, *Applied Physics Letters*, 92, 134102 (2008), © 2008 American Institute of Physics.

Van Neste et al., *Standoff photoacoustic spectroscopy*, Applied Physics Letters, 92; 2008; pp. 1-3.

Uotila et al., *Fourier Transform Infrared Measurement of Solid-, Liquid-, and Gas-Phase Samples with a Single Photoacoustic Cell*; Applied Spectroscopy; vol. 62, No. 6; 2008; pp. 655-659.

Tetard et al., *Elastic phase response of silica nanoparticles buried in soft matter*; Applied Physics Letters 93; 133113 (Published on-line Oct. 2, 2008); pp. 133113-1-133113-3.

*First helium microscope is put through paces at NIST*; R&D Mag (Sep. 3, 2008); pp. 1-2; www.rdmag.com/News/2008/09/First-helium—microscope-is-put-through-paces-at-NSIT.

*WITec Microscope Technology Win Prestigious 2008 R&D 100*; Chemie.De (Jul. 10, 2008); www.chemie.ded/news/e/84528.

*WITec Microscope Technology Wins Prestigious 2008 R&D 100 Award*; WITec; Jul. 2008 www.witec.de/en/company/witecnews/news.php?id=37.

ORNL Demonstrates Super-Sensitive Explosives Detector, Oakridger.com, Jun. 30, 2008.

Tetard et al.,; *Imaging nanoparticles in cells by nanomechanical holography*; Nature Nanotechnology Letters (Jun. 22, 2008); pp. 501-505; www.nature.com/naturenanotechnology.

Uotila, J., *A new design of the differential photoacoustic gas detector combined with a cantilever microphone*, The European Physical Journal, Special Topics, vol. 153, Mar. 12, 2008, pp. 401-404.

Sievilia et al., *Fabrication and characterization of an ultrasensitive acousto-optical cantilever*; Journal of Micromechanics and Microengineering; 17; 2007; pp. 852-859.

Lindley et al., *sensitivity comparison of three photoacoustic cells containing a single microphone, a differential dual microphone or a cantilever pressure sensor*; Applied Physics B, Lasers and Optics; 86; 2007; pp. 707-713.

Koskinen et al., *Cantilever enhanced photoacoustic detection of carbon dioxide using a tunable diode laser source*, Applied Physics B, Lasers and Optics, vol. 86, No. 3, Jan. 23, 2007, pp. 451-454.

Koskinen et al., *Extremely sensitive trace gas analysis with modern photoacoustic spectroscopy*; Science Direct, Vibrational Spectroscopy; 42; 2006; pp. 239-242.

Waghe et al., Infrared Study of UV-Irradiated Tungsten Trioxide Powders Containing Adsorbed Dimethyl Methyl Phosphonate and Trimethyl phosphate, *Res. Chem Intermed*, vol. 32, No. 7, pp. 613-623 , 2006.

Wouters et al., *Automated Scanning Probe Microscopy for Combinatorial Polymer Research*; Mater.Res.Soc.Symp.Proc.vol. 894 (2006), pp. 111-117.

Shekhawat et al., *Nanoscale Imaging of Buried Structures via Scanning Near-Field Ultrasound Holography*; Science Mag; vol. 310; Oct. 7, 2005; www.sciencemag.org; pp. 89-92.

Kosterev et al., *Applications of quartz tuning forks in spectroscopic gas sensing*, Review of Scientific Instruments, vol. 76, No. 4, Mar. 23, 2005, pp. 043105-1 043105-9.

Ledermann et al., *Piezoelectric $Pb(Zr_x, Ti_{1-x})O3$ thin film cantilever and bridge acoustic sensors for miniaturized photoacoustic gas detectors*; Journal of Micromechanics and Microengineering; 14; 2004; pp. 1650-1658.

Su et al., *Quartz tuning fork biosensor*, Biosensors and Bioelectronics, Elsevier, vol. 17, No. 1/02, Jan. 1, 2001, pp. 111-117.

Cuberes et al.; *Heterodyne force microscopy of PMMA/rubber nanocomposites: nanomapping of viscoelastic response at ultrasonic frequencies*; J. Phys.D: Appl. Phys. 33 (2000); pp. 2347-2355.

Wells, P. N.T., *A Vital Diagnostic Tool that Has Great Opportunities for Further Development*; IEEE Engineering in Medicine and Biology; Sep./Oct. 2000; pp. 14-20.

Crippa et al., C.; *Time-resolved photoacoustic spectroscopy: new developments of an old idea*; New Trends in Photobiology (Invited Review); 24; 1994; pp. 3015.

Kolosov et al., *Nonlinear Detection of Ultrasonic Vibrations in an Atomic Force Microscope*; Jpn. J. Appl. Phys. vol. 32 (1993); pp. L 1095-L 1098.

Yang et al., H.L., In Situ Diffuse Reflectance Infrared Spectroscopic Study of the Photodecomposition of Dibenzyl Ketone Adsorbed on Zeolites, *J. Phys. Chem*, 90, pp. 2422-2424, 1986.

* cited by examiner

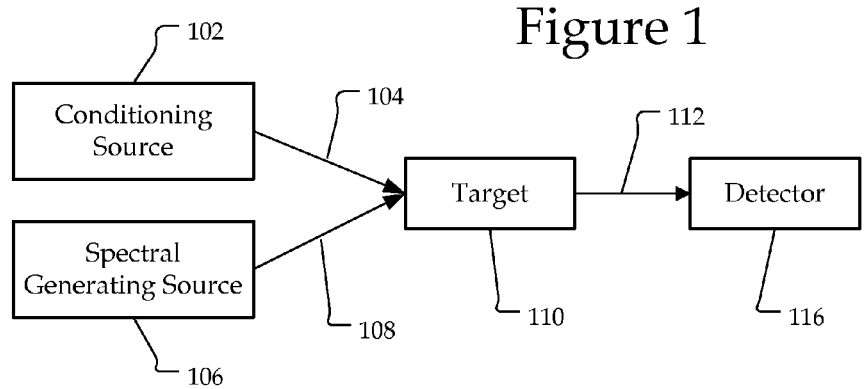
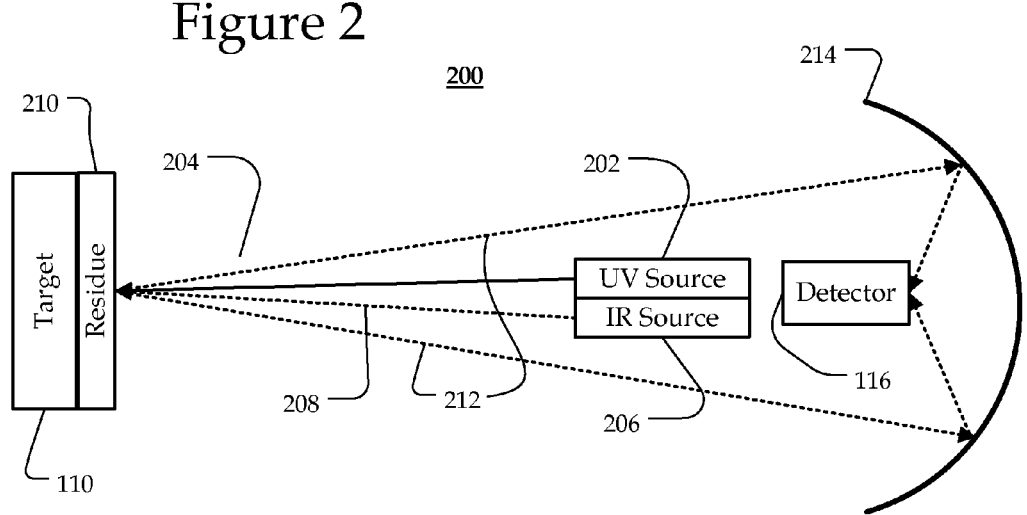

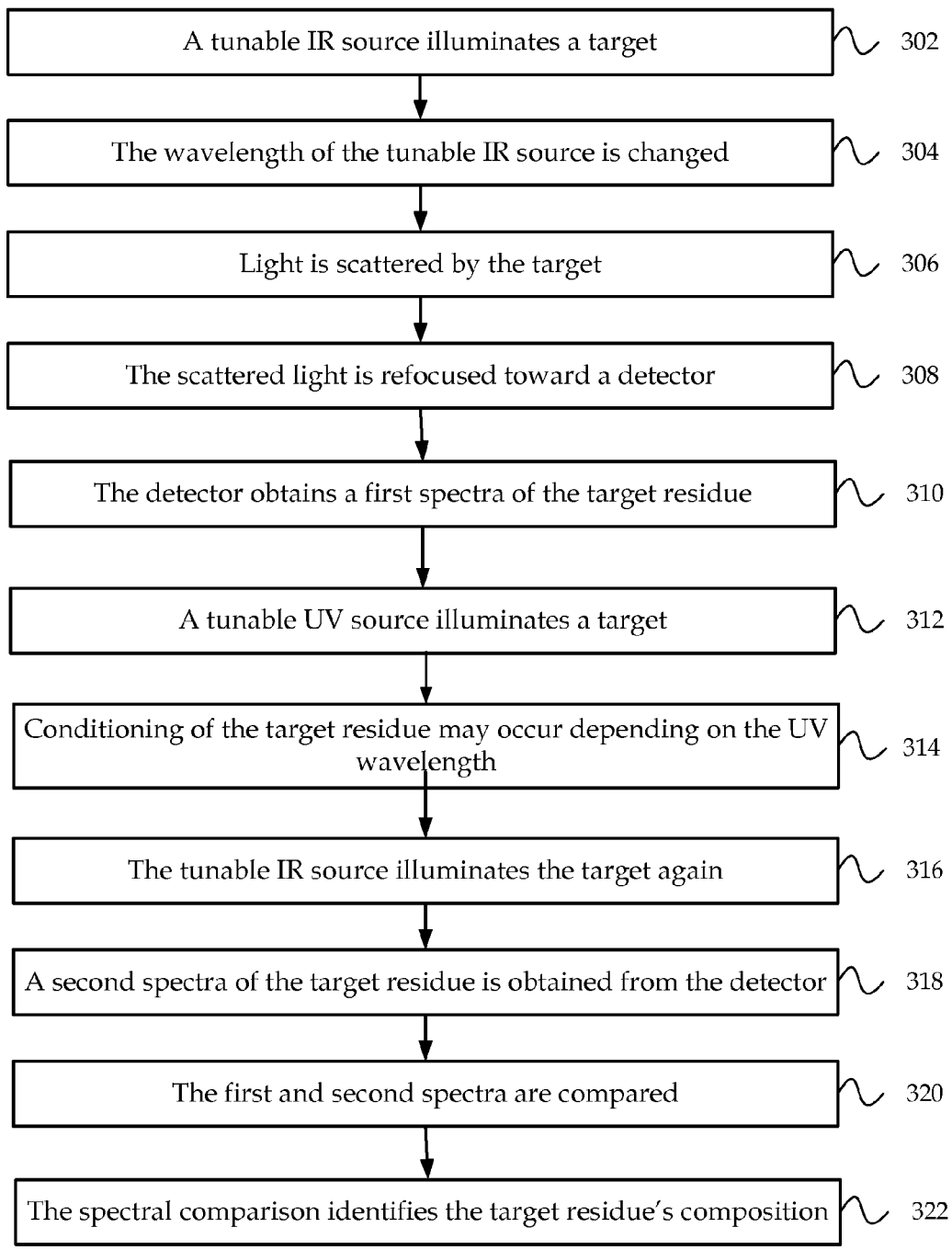

RDX Spectrum on a Car Fender

STANDOFF SPECTROSCOPY USING A CONDITIONED TARGET

STATEMENT REGARDING FEDERALLY SPONSORED RESEARCH

This invention was made with government support under Contract No. DE-AC05-000R22725 awarded by the U.S. Department of Energy. The government has certain rights in the invention.

BACKGROUND

Spectroscopy methods detect and generate a spectrum for a target. The target may be modified, such as with laser induced fluorescence (LIF), to partially vaporize the target and a spectrum may be measured from the resulting vapor. Based on the spectrum, some of the properties of the target material may be identified. Other spectroscopy methods cannot be utilized in a standoff manner and some cannot resolve small target residues. The LIF method analyzes the optical excitation of only by-products generated from a surface residue, which may prevent the measuring of a unique spectrum.

BRIEF DESCRIPTION OF THE DRAWINGS

The system and method may be better understood with reference to the following drawings and description. Non-limiting and non-exhaustive embodiments are described with reference to the following drawings. The components in the drawings are not necessarily to scale, emphasis instead being placed upon illustrating the principles of the invention. In the drawings, like referenced numerals designate corresponding parts throughout the different views.

FIG. 1 illustrates an exemplary spectroscopy system;

FIG. 2 illustrates an exemplary standoff spectroscopy system;

FIG. 3 illustrates a process for standoff spectroscopy;

DETAILED DESCRIPTION

Figure 4:
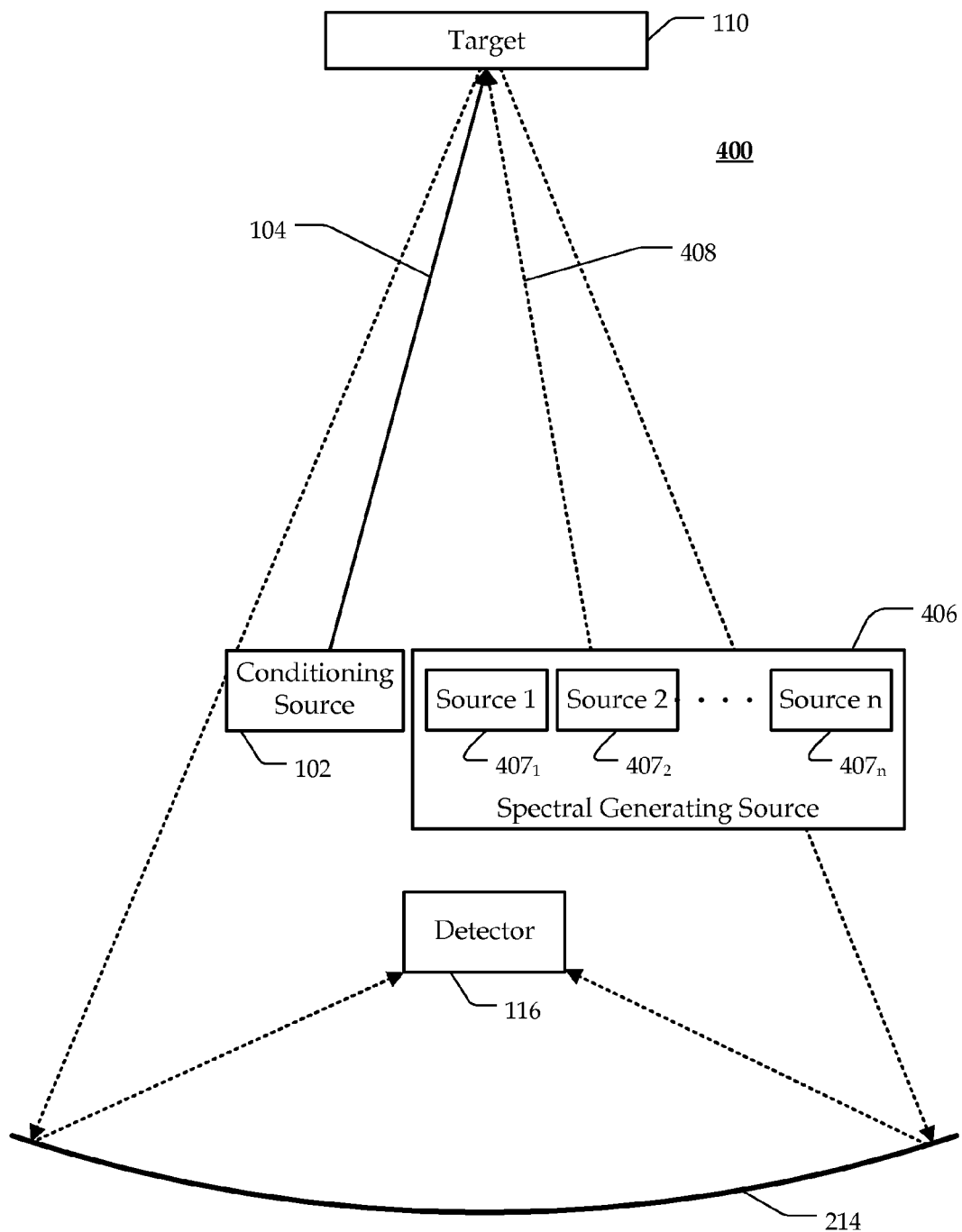
FIG. 4 illustrates an alternative exemplary embodiment of a standoff spectroscopy system.

By way of introduction, a system and method for standoff spectroscopy is disclosed. The system can detect molecules (e.g. in a residue) on a surface from a distance. A conditioning source emits radiation that modifies the residue, such as through decomposition. A spectral generating source measures a spectrum of the residue before and after the residue is exposed to the radiation from the conditioning source. The two spectra are compared to produce a distinct identification of the residues on the surface or identify certain properties of the residue. In one embodiment, the conditioning source is an ultraviolet source and the spectral generating source is an infrared source. Either of the sources may be tunable to target certain properties of the residue. For example, a particular molecule may decompose at a certain ultraviolet wavelength, so when the conditioning source emits ultraviolet radiation at that wavelength, that molecule may be detected by comparing spectra before and after the ultraviolet exposure.

FIG. 1 illustrates an exemplary spectroscopy system. The system utilizes a detector 116 to measure data about a target 110. The system includes a conditioning source 102 that emits radiation 104 at the target 110. A spectral generating source 106 emits radiation 108 at the target 110 that is measured by the detector 116 for determining a spectrum of the target.

The target 110 may comprise a substance that is measured from a distance. The target may be analyzed without contact for the measurement. The target 110 may be a solid, liquid, or gas on or near a surface. In one embodiment discussed with respect to FIG. 2, the target 110 may be a residue or residue(s) disposed on a surface of the target 110. For example, explosive or gun powder residue may be the target 110 to be identified. The target 110 may include a surface at an airport that is tested for explosive and/or other material residues. Alternatively, the target 110 may be human tissue or cells, such that a medical doctor may test for skin cancer or other skin conditions by analyzing a spectrum of light reflected off the skin. The spectra for cancer cells may be different from the spectra for normal cells. In another example, colon cancer may be detected when light is pumped through fiber optics along a colonoscopy tube. The doctor may view the abnormal areas and receive a confirmation using the spectra. This may be beneficial for testing lesions that are flat (early stages of colon cancer). The target 110 may include any chemical substance.

Either the spectral generating source 106 or the conditioning source 102 may include a beamformer or a light source, such as a laser, monochromator, light emitting diode (LED), diode laser, LED pile, or the sun with a grating or etalon. The sources 102, 106 may be tunable to modify the frequency, wavelength, or color of the emitted radiation.

The spectral generating source 106 emits radiation 108 that is scattered by the target 110. The radiation 108 may include a light beam of any type or a laser emission, such as infrared, visible, or gamma waves. Alternatively, the emission may include ultrasonic or microwave. The scattered radiation may be the result of the radiation 108 being reflected, diffracted, and/or rejected by the target 110. The scattered radiation 112 is measured by the detector 116. The detector 116 may be configured to measure radiation of the type emitted by the spectral generating source 106. For example, when the spectral generating source 106 is an IR source, the detector 116 is an IR detector. The detector 116 may analyze the scattered radiation 112 to produce a spectrum of the target 110. Changing the wavelength of the emitted radiation 108 may result in a change in wavelength or other properties of the scattered radiation 112. As the target 110 reflects, refracts, or scatters the changing wavelength of the radiation 108, the intensity of the scattered radiation 112 may also change.

The conditioning source 102 is configured to cause a reaction at the target 110 when the radiation 104 is transmitted to the target 100. The reaction is the conditioning of the target 110 and may further include decomposition, sublimation/vaporization, bleaching, absorption enhancing of the spectral generating source, or other reactions. In one embodiment, the reaction may comprise a decomposition of certain molecules at the target 110. The wavelength of the radiation 104 may be tuned or modified, which results in different reactions at the target 110. For example, different wavelengths of the emitted radiation 104 may cause certain molecules at the target 110 to decompose and other molecules may remain unaffected. Likewise, the emitted radiation 104 may cause sublimation of residue molecules at the target 110. The conditioning source 102 emits ultraviolet radiation 104 in one example or any type of electromagnetic radiation beam or a laser emission in other examples.

As described below with respect to FIG. 3, a spectrum of the target 110 is measured both before and after the target 110 is subjected to radiation from the conditioning source 102. The before and after spectra are differentially compared to analyze the makeup of the target 110. The comparison may include dividing the signals or performing other algorithms or Fourier transforms on the spectra to analyze the distinctions. By comparing a spectrum before the reaction with a spectrum after the spectrum, the target 110 may be identified. The analysis or comparison of spectra may occur at the detector 116, or the detector 116 may be coupled with an analysis apparatus, such as a computer system for analyzing the signals of the detector 116. The analysis may include a comparison of the measured spectrum before and after the conditioning source 102 emits radiation at the target 110. The difference in the target 110 spectra before and after that radiation 104 may identify which materials or molecules are present at the target 110. This comparison and analysis may be performed by a computer system (not shown) that includes a computer readable medium stored in a memory that includes instructions operable by a processor.

The computer system and process that analyses the spectra may be encoded in a signal bearing medium, a computer readable medium such as a memory, programmed within a device such as one or more integrated circuits, and one or more processors or processed by a controller or a computer. If the methods are performed by software, the software may reside in a memory resident to or interfaced to a storage device, synchronizer, a communication interface, or non-volatile or volatile memory in communication with a transmitter. A circuit or electronic device designed to send data to another location. The memory may include an ordered listing of executable instructions for implementing logical functions. A logical function or any system element described may be implemented through optic circuitry, digital circuitry, through source code, through analog circuitry, through an analog source such as an analog electrical, audio, or video signal or a combination. The software may be embodied in any computer-readable or signal-bearing medium, for use by, or in connection with an instruction executable system, apparatus, or device. Such a system may include a computer-based system, a processor-containing system, or another system that may selectively fetch instructions from an instruction executable system, apparatus, or device that may also execute instructions.

A "computer-readable medium," "machine readable medium," "propagated-signal" medium, and/or "signal-bearing medium" may comprise any device that includes, stores, communicates, propagates, or transports software for use by or in connection with an instruction executable system, apparatus, or device. The machine-readable medium may selectively be, but not limited to, an electronic, magnetic, optical, electromagnetic, infrared, or semiconductor system, apparatus, device, or propagation medium. A non-exhaustive list of examples of a machine-readable medium would include: an electrical connection "electronic" having one or more wires, a portable magnetic or optical disk, a volatile memory such as a Random Access Memory "RAM", a Read-Only Memory "ROM", an Erasable Programmable Read-Only Memory (EPROM or Flash memory), or an optical fiber. A machine-readable medium may also include a tangible medium upon which software is printed, as the software may be electronically stored as an image or in another format (e.g., through an optical scan), then compiled, and/or interpreted or otherwise processed. The processed medium may then be stored in a computer and/or machine memory.

FIG. 2 illustrates an exemplary standoff spectroscopy system 200. An ultraviolet ("UV") source 202 and an infrared ("IR") source 206 emit radiation 204, 208 respectively, at a residue 210. In this embodiment, the UV source 202 is one example of a conditioning source 102, and the IR source 206 is one example of the spectral generating source 106. The radiation is scattered 212 to collection optics 214 that focus the scattered radiation at the detector 116. This embodiment may be referred to as standoff IR spectroscopy with UV photodecomposition. The emitted radiation 204 from the UV source 202 may induce a reaction, such as photodecomposition of the residue 210 at the target 110. In other words, the residue 210 is conditioned by the emitted radiation 204 and that conditioning is used for identification purposes. The absorption of the UV light pulse may start a reaction, such as a photodecomposition process, that alters the target molecule's chemical structure by breaking them into smaller pieces. The radiation 204 comprises a light pulse at a specific or predetermined color. The UV color is chosen such that target molecules of the residue 210 will react to the UV irradiation 204.

A spectrum before and after the UV irradiation is taken. The IR irradiation 208 from the IR source 206 is scattered from the residue 210 or the target 110. The scattered radiation 212 is focused by the collection optics 214 towards the detector 116. The collection optics 214 may include a parabolic mirror, or a telescope, etc. and may be placed adjacent the sources at or near the collection optic's focal point. The detector 216 measures the spectrum of the residue 210. The spectrum before and after UV exposure is compared by the detector 116 or by a computer system that is coupled with the detector 116 or included as part of the spectroscopy system 200.

FIG. 3 illustrates a process for standoff spectroscopy. As described, FIG. 3 illustrates an exemplary process for UV photodecomposition standoff IR spectroscopy utilizing the spectroscopy system 200 from FIG. 2. Additional processes may be performed with the system 200 and the described process may be applicable to other embodiments. In block 302, a tunable IR source 206 illuminates a target 110. The wavelength of the tunable IR source 206 may be changed in block 304. The emitted radiation 208 from the tunable IR source 206 is scattered by the residue 210 and/or the target 110 in block 306. Collection optics 214 refocus the scattered light toward the detector 116 in block 308. By measuring the scattered light at the detector 116, a first spectrum of the residue 210 is obtained in block 310.

After the first spectrum is measured by the detector 116, the residue 210 is subjected to radiation 204 from a tunable UV source 202 in block 312. The radiation 204 causes a reaction, such as decomposition, that conditions the residue 210 depending on the UV wavelength in block 314. Different colors of UV radiation 204 may be utilized for measuring different molecules or properties of the residue 210. The UV source 202 may be tuned to emit a predetermined color or colors of UV radiation 204 for making specific measurements.

After the residue 210 is subjected to the UV source, the tunable IR source 206 again illuminates the target 110 in block 316. A second spectrum of the target 110 or the residue 210 is obtained from the detector 116 in block 318. A comparison of the first and second spectra is performed in block 320 using a computer system to analyze the differences. The differences in the spectra may identify the residue's composition in block 322.

FIG. 4 illustrates an alternative embodiment of a standoff spectroscopy system 400. In particular, the spectroscopy system 400 illustrates a spectral generating source 406 that comprises an array of sources $407_{1-n}$. The array source 406 may include a plurality of sources 407, such as a first source $407_1$, a second source $407_2$, and additional sources up to an $n^{th}$ source $407_n$. The value of n may be any integer greater than or equal to one. The array source 406 may also comprise a single source and an optical grating or a single source of all light colors. Each of the sources 407 may represent a different light source and/or a different color (wavelength) of emitted light or radiation. Each of the sources 407 may be modulated, pulsed, or chopped at a slightly different frequency to cover a range of frequencies. The array of sources 407 may be utilized when an individual source cannot change colors over a large range. The multiple sources in the array may cover a larger range to generate more spectra. The spectral generating source 406 may include a plurality of separate beams from each of the n sources 407. Alternatively, the spectral generating source 406 may include a beam emitted from each of the n sources 407. As discussed with respect to FIG. 6, there may be an array of detectors that match with the array of sources. The sources may cover varying portions of electromagnetic color spectrum (e.g. IR, X-ray, microwave, etc.) and the detector may be a broad detector (which detects all those color regions) or there may be an array of detectors to match the sources.

Figure 5:
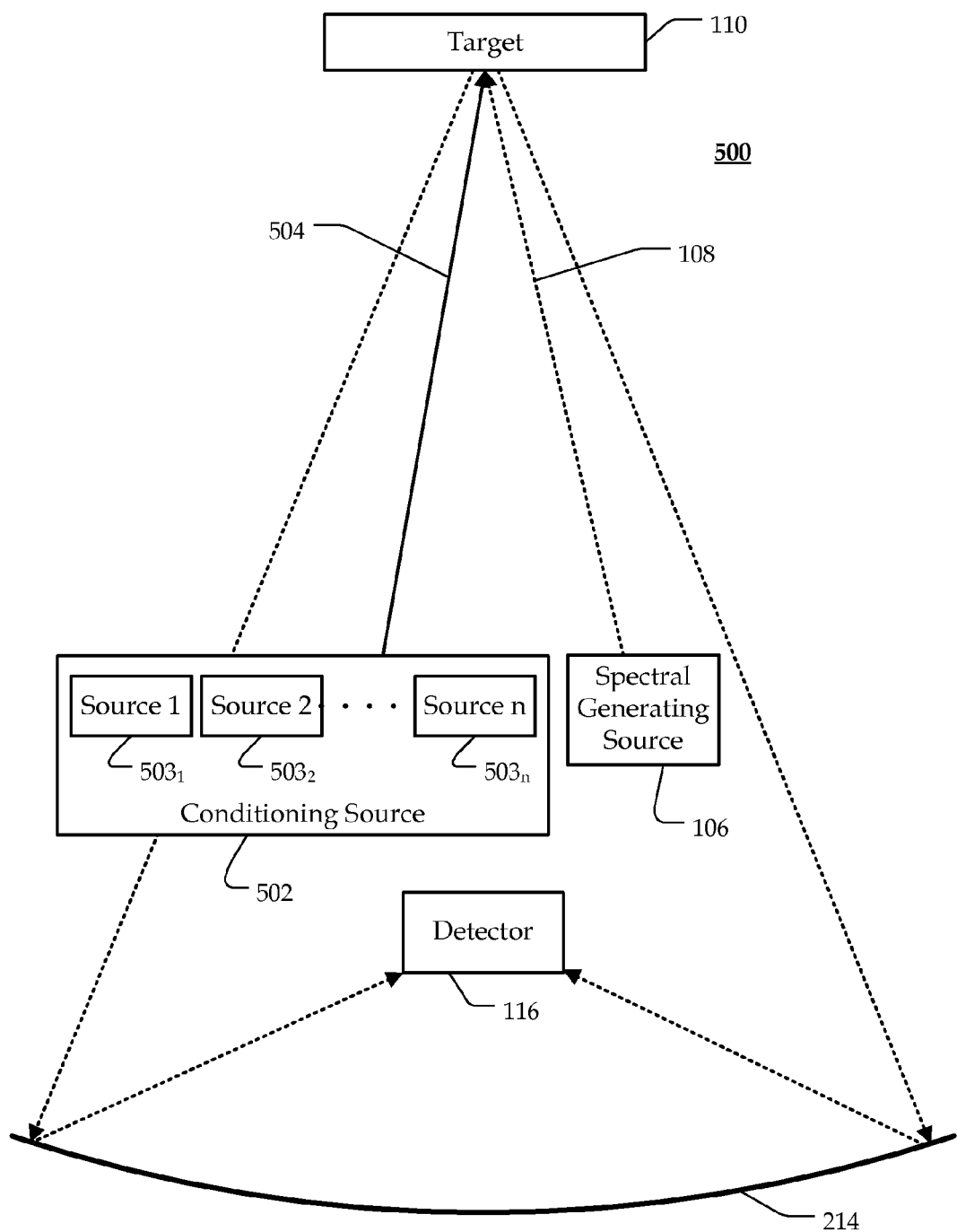
FIG. 5 illustrates an alternative exemplary embodiment of a standoff spectroscopy system.

FIG. 5 illustrates an alternative embodiment of a standoff spectroscopy system 500. In particular, the spectroscopy system 500 illustrates a conditioning source that comprises an array of sources $503_{1-n}$. The array of sources is similar to that shown in FIG. 4, except it is the conditioning source 502 that includes an array of sources in FIG. 5 rather than the spectral generating source 106. The array of sources $503_{1-n}$ may each emit radiation at a different wavelength. Accordingly, different sources from the array $503_{1-n}$ may be used for different wavelengths. Each wavelength may be predetermined for identifying a particular type of residue. In other words, multiple surface residues may be investigated with each source in the array generating a reaction from different types of residue.

Figure 6:
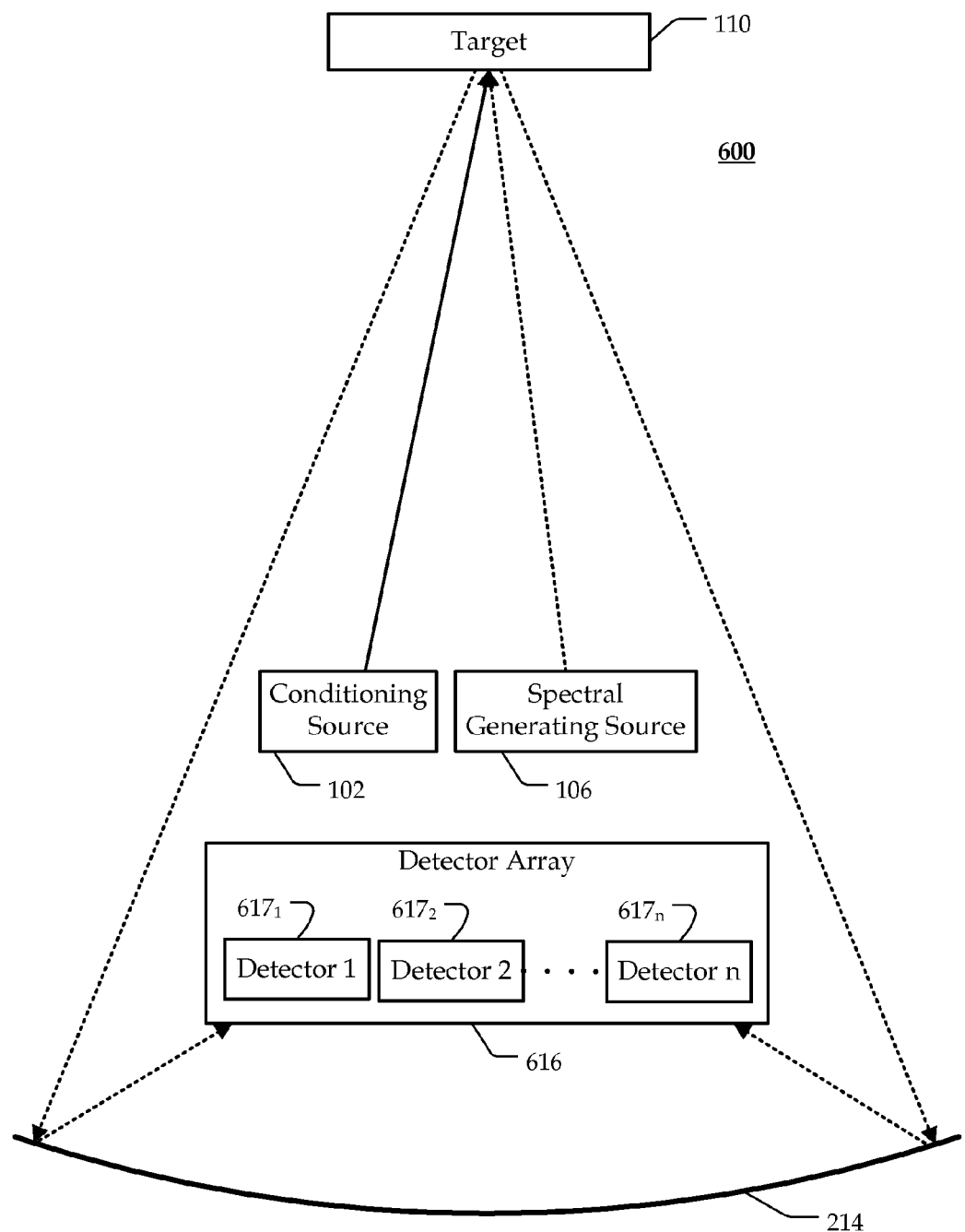
FIG. 6 illustrates an alternative exemplary embodiment of a standoff spectroscopy system.

FIG. 6 illustrates an alternative embodiment of a standoff spectroscopy system 600. The standoff spectroscopy system 600 illustrates a detector array 616 that comprises an array of detectors $617_{1-n}$ that each detect different radiation. In one embodiment, each of the detectors in the array 616 measures radiation at a different wavelength. In alternative embodiments, the detector array 616 may include a single detector that measures radiation at different wavelengths.

The systems shown in FIGS. 4-6 illustrate that any of the conditioning source 102, the spectral generating source 106, or the detector 116 may actually be an array rather than a single source/detector. Any combination of a single source/detector or an array of sources/detectors may be utilized. For example, the spectral generating source 106 may be tunable, rather than an array of sources, while the conditioning source may be an array of sources and the detector may be an array of detectors. Likewise, the spectral generating sources and the conditioning sources may be an array of tunable sources covering a larger electromagnetic range than a single tunable source may be able to cover.

Figure 7:
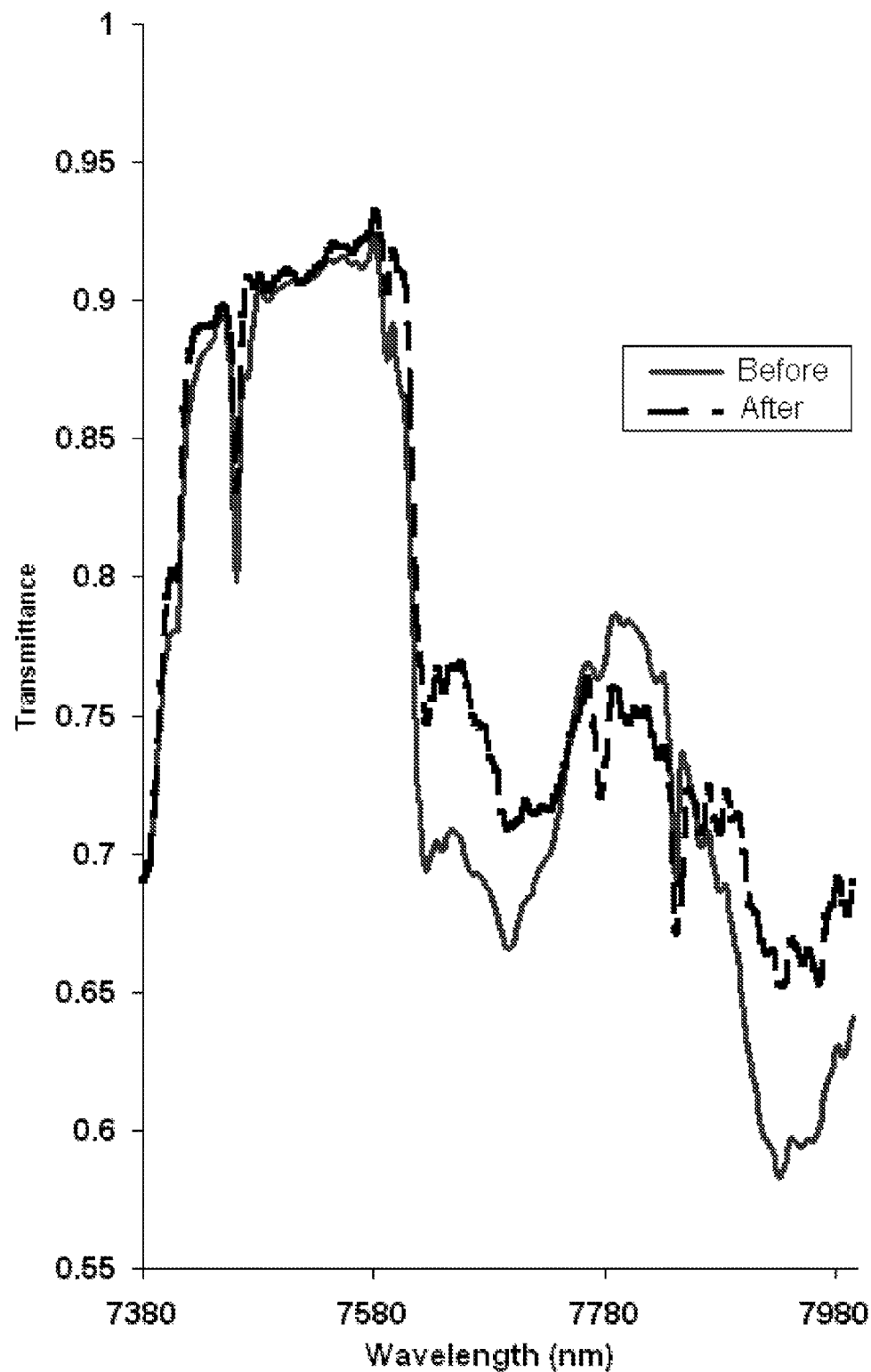
FIG. 7 illustrates an exemplary spectrum.

FIG. 7 illustrates an exemplary spectrum. The illustrated spectrum is of RDX on a car fender. The car fender may be the target 110 and the RDX molecules are the residue 210 on the surface of the target 110. RDX is cyclonite hexogen or T4 and is an explosive nitrosamine. It is a white crystalline powder that may be detected and identified using the above described spectroscopy systems and methods. In an RDX molecule, the nitro groups will absorb UV light at approximately 200-255 nanometers. UV light absorption by the nitro group will cause electronic transitions between its conjugated structures. Electrons reach higher energy levels which may cause chemical decomposition of RDX. FIG. 7 shows the IR standoff spectra of RDX before and after UV exposure on a surface. FIG. 7 shows a decrease in peak intensity especially in the absorption region of nitro group, which suggests that nitro groups in RDX molecule are being chemically decomposed by UV radiation. The difference between the spectrum before and after UV yields the transmittance signature of RDX.

Figure 8:
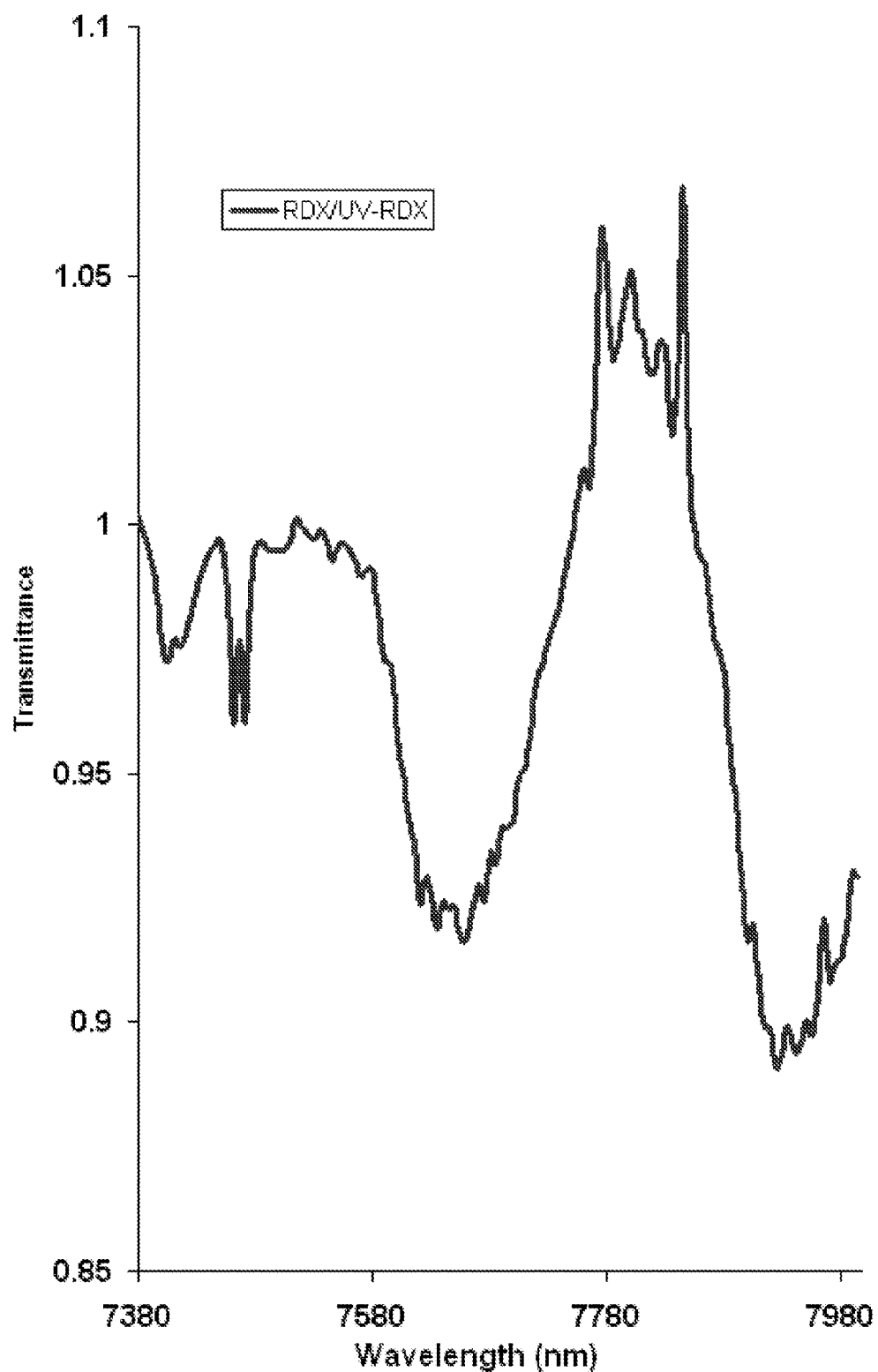
FIG. 8 illustrates an exemplary spectrum comparison.

FIG. 8 illustrates an exemplary spectrum comparison. It illustrates a comparison of the spectra measured before and after UV exposure of RDX. In particular, FIG. 8 is the second IR spectrum divided by the first IR spectrum, where the second IR spectrum is generated following UV exposure. The downward peaks in FIG. 8 corresponding to the wavelength of 7400 nanometers, 7600 nanometers, and 7900 nanometers may represent specific absorption characteristics of RDX. A clean car fender would not exhibit downward absorption peaks using the exemplary spectrum comparison, but the presence of RDX results in these peaks as shown in FIG. 8.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The above disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description. While various embodiments of the invention have been described, it will be apparent to those of ordinary skill in the art that many more embodiments and implementations are possible within the scope of the invention. Accordingly, the invention is not to be restricted except in light of the attached claims and their equivalents.

We claim:

1. A system for standoff spectroscopy to analyze a residue comprising:
a target surface for spectral analysis;
an infrared ("IR") source that irradiates the target surface with IR radiation;
a detector that measures a spectrum from the target surface based on the IR radiation;
an ultraviolet ("UV") source that irradiates the target surface with UV radiation, wherein the detector measures a first and second spectrum of the target surface away from the target surface based on radiation from the infrared source, wherein the second spectrum is measured by the detector after the ultraviolet source irradiates the target surface; and
a processor coupled with the detector and configured to perform the spectral analysis by comparing the first and second spectrum, wherein the spectral analysis determines whether the residue is present on the target surface based on the comparison of the first and second spectrum.

2. The system of claim 1 further comprising:
a collection optic configured to receive scattered radiation from the target surface and refocus the scattered radiation to the detector, wherein the IR radiation is scattered at the target surface to result in the scattered radiation.

3. The system of claim 1 wherein the spectral analysis comprises identifying wavelengths at which the UV radiation reacted with the residue.

4. A method for identifying a residue on a surface with standoff spectroscopy comprising:
detecting a first spectral measurement at the surface;
irradiating the surface with conditioning radiation at a predetermined frequency for causing a reaction with the residue on the surface;
detecting a second spectral measurement at the surface after the surface has received the conditioning radiation; and
comparing the second spectral measurement with the first spectral measurement to determine a presence of the residue by identifying wavelengths at which the conditioning radiation reacts with the residue.

5. The method of claim 4 wherein the detecting a first and second spectral measurement comprises:
emitting radiation from a spectral generating source towards the surface;
scattering the radiation from a spectral generating source;
collecting the scattered radiation from the surface; and
measuring the scattered radiation from the surface to generate the spectral measurement.

6. The method of claim 5 wherein the scattered pulsed light is reflected or refracted from the target.

7. The method of claim 5 wherein the radiation from the spectral generating source comprises infrared radiation.

8. The method of claim 4 wherein the conditioning radiation comprises ultraviolet radiation and the reaction comprises a decomposition of the residue caused by the ultraviolet radiation.

9. The method of claim 4 wherein the comparison comprises dividing the first spectrum from the second spectrum to identify the wavelengths at which the conditioning radiation reacted with the residue.

10. The method of claim 4 wherein the identified wavelengths correspond with particular residues such that an identification of a wavelength can identify the residue.

11. The method of claim 10 wherein the predetermined frequency of the radiation corresponds with a particular residue that is to be identified.

12. The method of claim 4 wherein the comparison is performed using a processor that accesses the first and second spectrums which are stored in a memory.

13. A system for standoff spectroscopy of a residue comprising:
a spectral generating source configured to emit a first type of radiation;
a target comprising the residue on a surface of the target;
a conditioning source configured to emit a second type of radiation to react with the residue on the surface, wherein the reaction modifies a spectrum of the residue on the surface;
a detector configured to measure a first spectrum from the spectral generating source and to measure a second spectrum from the spectral generating source, wherein the second spectrum is measured after the conditioning source after the reaction with the emitted second type of radiation; and
a processor configured to identify the residue by comparing the second spectrum with the first spectrum.

14. The system of claim 13 further comprising:
a collection optic that focuses the first type of radiation onto the detector for measuring the first and second spectrums.

15. The system of claim 13 wherein the analysis of the residue by the processor comprises identifying wavelengths at which the second type of radiation reacts with the residue.

16. The system of claim 15 wherein the comparison comprises dividing the first spectrum from the second spectrum to identify the wavelengths at which the conditioning radiation reacted with the residue.

17. The system of claim 13 wherein the reaction comprises decomposition, sublimation, vaporization, bleaching, absorption, or another response by the residue.

18. The system of claim 13 wherein the comparison is configured to identify the residue based on differences in the second spectrum from the first spectrum.

19. The system of claim 13 wherein the second type of radiation is at a predetermined wavelength, further wherein that predetermined wavelength is known to cause a reaction with certain molecules in the residue.

20. The system of claim 19 wherein evidence of the reaction signifies the presence of the certain molecules in the residue.

* * * * *